US008211479B2

(12) United States Patent
Bombardelli

(10) Patent No.: US 8,211,479 B2
(45) Date of Patent: Jul. 3, 2012

(54) COMBINATIONS OF VASOACTIVE SUBSTANCES WITH ESTROGENS AND THEIR USE IN THE TREATMENT OF FEMALE SEXUAL DYSFUNCTIONS

(75) Inventor: Ezio Bombardelli, Groppello Cairoli (IT)

(73) Assignee: Indena S.p.A., Milan (IT)

( * ) Notice: Subject to any disclaimer, the term of this patent is extended or adjusted under 35 U.S.C. 154(b) by 100 days.

(21) Appl. No.: 12/667,392

(22) PCT Filed: Jun. 26, 2008

(86) PCT No.: PCT/EP2008/005191

§ 371 (c)(1), (2), (4) Date: Mar. 29, 2010

(87) PCT Pub. No.: WO2009/003631

PCT Pub. Date: Jan. 8, 2009

(65) Prior Publication Data

US 2010/0183751 A1 Jul. 22, 2010

(30) Foreign Application Priority Data

Jul. 3, 2007 (EP) .................................... 07012989

(51) Int. Cl.
*A61K 36/00* (2006.01)

(52) U.S. Cl. ...................................................... 424/725

(58) Field of Classification Search ........................ None
See application file for complete search history.

(56) References Cited

U.S. PATENT DOCUMENTS

| | | | |
|---|---|---|---|
| 6,623,768 | B1 | 9/2003 | Naguib |
| 2005/0100618 | A1 | 5/2005 | Thompson et al. |

FOREIGN PATENT DOCUMENTS

| | | | |
|---|---|---|---|
| WO | WO 2005/004858 | * | 1/2005 |
| WO | WO 2005/004890 A1 | * | 1/2005 |

OTHER PUBLICATIONS

FitzSimmons. *Ferula hormonis* (The Lebanese Viagra). Dec. 5, 2003 Retrieved from the Internet. <http://web.archive.org/web/20031205124538/http://www.gcwhite.co.u k/Ferula.htm >.*

Jain et al. Constitution and synthesis of naturally occurring isopentenylated kaempferol derivatives, noranhydroicaritin and isoanhydroicaritin and related flavonols including di-O-methylicaritin. Australian Journal of Chemistry (1975), 28(3), 607-19.*

International Search Report, dated Nov. 27, 2008, from corresponding PCT application.

Stuart Fitzsimmons, "*Ferula hormonis* (The Lebanese Viagra)", Dec. 5, 2003, retrieved from the Internet: http://web.archive.org/web/20031205124538/http://www.gcwhite.co.uk/Ferula.htm.

* cited by examiner

*Primary Examiner* — Melenie McCormick
(74) *Attorney, Agent, or Firm* — Young & Thompson

(57) ABSTRACT

Compositions comprising:
- vasokinetic natural coumarins or extracts containing them;
- anti-phosphodiesterase agents selected from 3,7-O-di-(2-hydroxyethyl)icaritin or 7-O-hydroxyethyl-icariside II and/or forskolin or extracts containing them;
- phytoestrogens selected from ferutinine or ferutinine-containing extracts of *Ferula* sp. or p-pivaloylferutinine.

17 Claims, No Drawings

COMBINATIONS OF VASOACTIVE SUBSTANCES WITH ESTROGENS AND THEIR USE IN THE TREATMENT OF FEMALE SEXUAL DYSFUNCTIONS

SUMMARY

This invention concerns a combination of substances acting on peripheral blood circulation with vegetable estrogens that are useful in the treatment of sexual dysfunctions associated with reduced orgasm and/or insufficient vaginal lubrication. The active ingredients have been selected from some coumarins and diterpenes, or extracts containing them, as well as flavonoids exerting a specific anti-phosphodiesterase activity. The combination of these substances is incorporated into suitable formulations, to be applied to female genitalia, comprising excipients aiding rapid absorption of the active ingredients and contributing to improving orgasm and sexual performance as well as inducing desire.

This invention concerns compositions comprising a combination of substances acting on peripheral blood circulation with vegetable estrogens. The compositions of the invention are useful in the treatment of sexual dysfunctions associated with reduced orgasm and/or insufficient vaginal lubrication.

BACKGROUND OF THE INVENTION

The loss of, or poor, erectile capability and lubrication, of different origin and intensity, is a very serious problem in an increasingly larger number of women, with unfavourable effects on couple relations. A sense of frustration, with a tendency to stop sexual intercourses, affects a large number of women, whether in young age or after the menopause. These problems, which were ignored until a few decades ago for cultural, religious or other reasons, are now discussed with the family doctor both thanks to the advent of women emancipation and to the introduction of vasoactive substances in the treatment of male impotence.

The interest of endocrinologists, gynecologists and sexologists for female sexual dysfunction is justified by the high demand for drugs or alternative aids. The great difficulties to solve these problems in this approach consist in the lack of suitable markers capable of differentiating the dysfunctions, or the lack of diagnostic references capable of distinguishing a frequently psychic dysfunction from a real disease. A number of patients often undergo non-validated diagnostic procedures and receive generic pharmacological treatments that are useful for other diseases rather than for these dysfunctions. Very little research has been until now carried out to investigate the biochemical processes and hormonal relations linked to the onset of orgasm. Sexual activity is linked to different cognitive, emotional and, finally, organic factors. None of these parameters, investigated separately, has proved to be exhaustive, and so their combination has to be submitted to careful examination to find useful products. After the discovery of the male functional mechanisms, linked to the vascular component, research turned to this direction also in women. The locoregional microcirculation was chosen as the evaluation criterion in consideration of the extreme importance of this parameter for a satisfactory sexual life.

It was surprising to find that, contrary to man, the substances affecting vasomotion alone, as well as phosphodiesterase inhibitors, are not sufficient to normalize the sexual intercourse in women, as it involves secretive problems the do not depend on the erectile function of the sexual organs.

DESCRIPTION OF THE INVENTION

It has now been found that optimization of the sexual intercourse, improving libido and physiological lubrication, is substantially obtained by means of the topical application of a combination of substances activating arterial circulation and venous expansion through specific phosphodiesterase inhibition with estrogens.

The compositions of the invention comprise:

vasokinetic natural coumarins;

anti-phosphodiesterase agents selected from 3,7-O-di-(2-hydroxyethyl)icaritin or 7-O-hydroxyethyl-icariside II and/or forskolin or extracts containing them;

phytoestrogens selected from ferutinine or ferutinine-containing extracts of *Ferula* sp. or p-pivaloylferutinine.

The invention also refers to the use of said combination for the preparation of a medicament or medical device for the treatment of female sexual dysfunction.

Vasokinetic natural coumarins are preferably esculetin, esculoside and visnadin, more preferably esculoside or visnadin. Extracts comprising these compounds may be used as an alternative to, the pure compounds.

Said vasokinetic agents increase loco-regional blood flow in the corpora cavernosa and enable relaxation of smooth muscles; this action causes enlargement of cavernous sinusoids to leave room for affluent blood and, therefore, intumescence. This intumescence of the corpora cavernosa results in the compression of the surrounding veins, thus preventing blood from draining out from the corpora cavernosa.

Visnadin is a coumarin mainly found in the seeds of *Ammi visnaga*—a plant that has been traditionally used in treatment of anginal disorders. The compound has been widely used in the pharmaceutical field as a coronary dilator. When topically administered, this compound exerted a marked vasokinetic action on arterioles and precapillary arteries by increasing blood flow and tissue perfusion (EP 0 418 806). The supply of arterial blood to erectile tissues starts tumescence and maintains it over time through the pumping function in arteries and arterioles for periods of one to three hours. Visnadin also exerts anti-phosphodiesterase action, maintaining cyclic nucleotides.

Esculoside is a coumarin found in a number of plants, such as *Aesculus hippocastanus, Fraxinus communis*, etc. and has vasokinetic effects affecting veins as well as arteries. Esculoside and extracts containing it are commercially available.

Forskolin is a labdane diterpene found in the Indian plant *Coleus forskohlii*. Forskolin and/or forskolin-containing extracts are agonists of adenylate cyclase. This enzyme converts ATP into cyclic AMP (cAMP), which, in turn, causes intracellular calcium concentration to decrease and the smooth muscles to relax. Forskolin purified extracts of *Coleus forskohlii* containing forskolin are commercially available.

3,7-O-di-(2-hydroxyethyl)icaritin (1) or 7-O-hydroxyethyl-icariside II (2), prepared according to example 4 and 5 respectively, are novel compounds and are also an object of the invention. They are powerful inhibitors of phosphodiesterase cGMP.

The table below shows cGMP phosphodiesterase activity of 1 and 2 in comparison with sildenafil.

| Compound | cAMP-PDE μM (mean value ± sd) | PDE5A1 μM (mean value ± sd) |
|---|---|---|
| 1 | 96.3 ± 12.9 | 0.074 ± 0.007 |
| 2 | 135.7 ± 14.2 | 0.36 ± 0.006 |
| Sildenafil | 27.6 ± 5.3 | 0.075 ± 0.004 |

High levels of cGMP maintain tumescence of erectile tissues after stimulation until orgasm is reached.

Ferutinine or ferutinine containing extract or p-pivaloylferutinine have an estrogenic action comparable to that of estradiol but without unwanted systemic effects. An example of a process for the preparation of ferutinine or ferutinine containing extract or p-pivaloylferutinine is reported in WO2004/087179.

Coumarins may be present in amounts ranging from 0.1 to 10% by weight, preferably from 0.2 to 1%.

Forskolin or extracts containing it may be present in amounts ranging from 0.01 to 2% by weight, preferably from 0.03 to 0.5%.

3,7-hydroxyethyl icaritin may be present in amounts ranging from 0.01 to 1% by weight, preferably from 0.1 to 0.5%.

Ferutinine or ferutinine-containing extracts may be present in amounts ranging from 0.01 to 2% by weight, preferably from 0.05 to 0.5%.

The active ingredients of the composition of the invention act synergistically to restore the performance of sexual organs.

The activity of this mixture of compounds takes place through the incretion or inhibition of mediators and receptors; for example, an important role in the tumescence of the corpora cavernosa is linked to acetylcholine—a well-known parasympathetic neurotransmitter that induces release of nitric oxide (NO), VIP and CGRP (calcitonin gene-related peptide) by nerve endings. NO release is responsible for a succession of events resulting in tumescence and orgasm.

The compositions of the invention were tested by evaluating the microcirculation of the clitoris and labia minora, as well the lubrication degree—evaluated in terms of response intensity and duration—following their topical application.

The formulations of this invention enhance sexual performance, in women. For example, a combination in the form of a gel containing visnadin 1%, coleus forskolin extract containing 80% of forskolin 0.25%, 3,7-O-di-(2-dihydroxyethyl) icaritin 0.2% and *ferula communis* extract containing 40% of ferutinine 0.25%, was administered in a group of 18 fertile female volunteers in an efficacy test, in which, apart from subjective data, blood flow parameters in the external genitalia were measured using a non-invasive method (Laser Doppler and Optical-probe Video capillaroscopy); in this test, the combination proved to be able to increase blood flow to 260% over the baseline value. The patients reported a general subjective sensation of well-being and sexual excitation within half an hour from the application. The single component tested separately increased the blood flow by about 20-25%. The formulation that proved to be very well accepted was a lipophilic gel as described in example 1; a suspension incorporated in soft gelatin capsules with a special fragile operculum is also of interest; when squeezed, the capsules release the fluid in the region of the clitoris and labia minora. These capsules contain 10 mg visnadin, 2 mg *Coleus forskohlii* extract with 80% forskolin, 5 mg 3,7-hydroxyethyl icaritin and 8 mg *Ferula communis* extract with 40% ferutinine (example 3). Single-dose sachets containing the same active ingredients or means allowing repeatable doses may also be an advantageous alternative to capsules.

The following examples illustrate the invention.

Example 1

Vaginal Gel

| | |
|---|---|
| Visnadin | 1% |
| *Coleous forskolii* extract >80% | 0.25% |
| 3,7-O-hydroxyethyl-ikaritina | 0.2% |
| *Ferula communis* extract 40% | 0.25% |
| Hydroxyethylcellulose | 3% |
| Polysorbate 80 | 3% |
| p-Hydroxy-Methylbenzoate | 0.1% |
| Propylene glycol. | to 100 |

Example 2

O/W Emulsion

| | |
|---|---|
| Visnadin | 10.0 mg |
| *Coleous forskolii* extract >80% | 2.0 mg |
| 3,7-O-hydroxyethyl-ikaritine | 5.0 mg |
| *Ferula communis* extract | 8.0 mg |
| Polyethylenglycol palmitoyl-stearate | 80.0 mg |
| Polyoxyethylene glycerides | 60.0 mg |
| Benzoic acid | 5.0 mg |
| Butylhydroxyanisole | 0.5 mg |
| Vaseline oil | 450.0 mg |
| Purified water. | to 3.0 g |

Example 3

Suspension for Soft Gelatin Capsules

| | |
|---|---|
| Visnadin | 10.0 mg |
| *Coleous forskolii* extract >80% | 2.0 mg |
| 3,7-O-hydroxyethyl-ikaritine | 5.0 mg |
| *Ferula communis* extract | 8.0 mg |
| Polisorbate | 100 mg |
| PEG 600 q.b. a | 600.0 mg |

Example 4

Preparation of 3,7-O-di-(2-hydroxyethyl)icaritin 145 g of potassium carbonate, 39 mL (68 g) of 2-bromoethanol and 5.4 g of tetrabutylammonium bromide were added to a solution of 27 g of Icaritin in 1.95 L of acetone. The reaction mixture was stirred at 40° C. for 20 hours and then filtered on buchner funnel. The cake was washed with acetone (300 mL). The organic phases were combined and evaporated under reduced pressure. The crude was dissolved in 250 mL of boiling acetonitrile, left to cool at room temperature and then refrigerated overnight at 4° C. The precipitated was filtered under reduce pressure and washed with 30 mL of acetone. The product was obtained as white solid (10 g).

$^1$H-NMR (DMSO-$d_6$) δ 1.65 (d, 3H); 1.77 (d, 3H); 3.51 (d, 2H); 3.68 (m, 2H); 3.78 (m, 2H); 3.89 (s, 3H), 4.12 (m, 4H);

4.80 (t, 1H); 4.89 (t, 1H); 5.20 (m, 1H); 6.57 (s, 1H); 7.15 (d, 2H); 8.19 (d, 2H), 12.7 (s, 1H).

Example 5

Preparation of 7-O-hydroxyethyl-icariside II 137.5 g of anhydrous potassium carbonate, 5 g tetrabutylammonium bromide and 35 mL of 2-bromoethanol were added to a suspension of 25 g of Icariside II in 3.12 L of acetone. The mixture was stirred at 40° C. After one day the reaction was completed. The crude mixture was filtered on Celite to remove inorganic salts; the cake was washed with acetone (100 mL) and with a methanol/acetone solution (1:10, 200 mL). The organic phases were collected and evaporated under reduced pressure. The residue (55 g) was dissolved in 1 L of ethyl acetate. The solution was washed two times (1 L and 0.3 L respectively) with water. The aqueous layers were extracted with 0.3 L of ethyl acetate. The organic layers were collected and washed another time with 0.2 L of water, dried over $Na_2SO_4$, filtered and evaporated under reduced pressure. The product was obtained as a white solid (14.3 g).

$^1$H-NMR (acetone-$d_6$) δ 0.85 (d, 3H); 1.61 (s, 3H); 1.72 (s, 3H); 3.21-3.75 (m, 5H); 3.81-3.90 (m, 2H); 3.92 (s, 3H); 3.94 (t, 2H); 4.21 (t, 2H); 5.15-5.26 (m, 1H); 5.47 (d, 1H); 6.47 (1H'); 7.14 (d, 2H); 7.95 (d, 2H).

MS m/z 581 (M+1). Mp 194-96 (ethanol).

The invention claimed is:

1. A compound 3,7-O-di-(2-hydroxyethyl)icaritin.

2. A composition comprising the compound of claim 1 and a pharmaceutically acceptable carrier.

3. The composition according to claim 2, wherein the 3,7-O-di-(2-hydroxyethyl)icaritin is present in an amount of 0.01% to 1% by weight.

4. The composition according to claim 2, wherein the 3,7-O-di-(2-hydroxyethyl)icaritin is present in an amount of 0.1% to 0.5% by weight.

5. The composition according to claim 2, further comprising a vasokinetic agent selected from the group consisting of: esculetin, esculoside and visnadin.

6. The composition according to claim 5, wherein the vasokinetic agent is present in an amount of 0.1% to 10% by weight.

7. The composition according to claim 5, wherein the vasokinetic agent is present in an amount of 0.2% to 1% by weight.

8. The composition according to claim 2, further comprising a phytoestrogen selected from the group consisting of: ferutinine and p-pivaloylferutinine.

9. The composition according to claim 8, wherein the phytoestrogen is present in an amount of 0.01% to 2% by weight.

10. The composition according to claim 8, wherein the phytoestrogen is present in an amount of 0.05% to 0.5% by weight.

11. The composition according to claim 5, further comprising forskolin.

12. The composition according to claim 11, wherein the forskolin is present in an amount of 0.01% to 2% by weight.

13. The composition according to claim 11, wherein the forskolin is present in an amount of 0.03% to 0.5% by weight.

14. The composition according to claim 5, further comprising:

a vasokinetic agent selected from the group consisting of: esculetin, esculoside and visnadin, forskolin, and a phytoestrogen selected from the group consisting of: ferutinine and p-pivaloylferutinine.

15. The composition according to claim 5, wherein the composition is in the form of a gel.

16. The composition according to claim 5, wherein the composition is in the form of an emulsion.

17. The composition according to claim 2, wherein the composition is in the form of a soft gelatin capsule.

* * * * *